United States Patent
Langereis et al.

(10) Patent No.: US 9,642,802 B2
(45) Date of Patent: May 9, 2017

(54) LIPID BILAYER CARRIER FOR DRUGS OR IMAGING AGENTS

(75) Inventors: Sander Langereis, Mierlo (NL);
Holger Gruell, Eindhoven (NL);
Mariska De Smet, Eindhoven (NL);
Erica Maria Gerarda Aussems-Custers, Helmond (NL);
Johan Lub, Valkenswaard (NL)

(73) Assignee: Koninklijke Philips N.V., Eindhoven (NL)

(*) Notice: Subject to any disclaimer, the term of this patent is extended or adjusted under 35 U.S.C. 154(b) by 782 days.

(21) Appl. No.: 13/809,469

(22) PCT Filed: Jul. 8, 2011

(86) PCT No.: PCT/IB2011/053047
§ 371 (c)(1),
(2), (4) Date: Jan. 10, 2013

(87) PCT Pub. No.: WO2012/007886
PCT Pub. Date: Jan. 19, 2012

(65) Prior Publication Data
US 2013/0108551 A1 May 2, 2013

(30) Foreign Application Priority Data

Jul. 13, 2010 (EP) .................................. 10169325

(51) Int. Cl.
*A61K 9/127* (2006.01)
*A61K 41/00* (2006.01)
*A61K 31/704* (2006.01)
*A61K 49/10* (2006.01)
*A61K 49/18* (2006.01)

(52) U.S. Cl.
CPC ............ *A61K 9/127* (2013.01); *A61K 31/704* (2013.01); *A61K 41/0028* (2013.01); *A61K 49/106* (2013.01); *A61K 49/1812* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos | |
| 6,726,925 B1 | 4/2004 | Needham | |
| 7,452,551 B1 * | 11/2008 | Unger | A61K 47/48238 424/1.11 |
| 2002/0102298 A1 | 8/2002 | Needham | |
| 2006/0057192 A1 | 3/2006 | Kane | |
| 2007/0077230 A1 | 4/2007 | Mon | |
| 2007/0077283 A1 | 4/2007 | Quay | |

FOREIGN PATENT DOCUMENTS

| | | |
|---|---|---|
| EP | 331504 A1 | 9/1989 |
| EP | 2067485 A1 | 6/2009 |
| JP | 2006306794 A | 11/2006 |
| WO | 9614057 A1 | 5/1996 |
| WO | 2010029469 A1 | 3/2010 |

OTHER PUBLICATIONS

Ipsen et al. Modelling the phase equilibria in two-component membranes of phospholipids with different acyl-chain lengths. 1998 Biochim. Biophys. Acta. 944: 121-134.*
Cevc G. How membrane chain-melting phase-transition temperature is affected by the lipid chain asymmetry and degree of unsaturation: an effective chain-length model. 1991 Biochemistry 30: 7186-7193.*
Mills, Jeffrey K. et al "Lysolipid Incorporation in Dipalmitorlphosphatidylcholine Bilayers Membranes Enhances the Ion Permeability and Drug Release Rates at the Membrane Phase Transition", Science Direct Biochimica et Biophysica Acta, vol. 1716, No. 2, Oct. 2005, pp. 77-96.
De Smet, Mariska et al "Temperature-Sensitive Liposomes for Doxorubicin Delivery under MRI Guidance", Journal of Controlled Release, vol. 143, No. 1, Apr. 2010, pp. 120-127.
Lindner, Lars H. et al "Dual Role of Hexadecylphosphocholine (miltefosine) in Thermosensitive Liposomes: Active Ingredient and Mediator of Drug Release", Science Direct, Journal of Controlled Release, vol. 125, (2008) pp. 112-120.
Bratton, Donna L. et al "Effects of Platelet Activating Factor and Related Lipids on Phase Transition of Dipalmitoylphosphatidylcholine", Biochimica et Biophysica Acta, vol. 941, 1988, pp. 76-82.
Needham, David et al "A New Temperature-Sensitive Liposome for use with Mild Hyperthermia: Characterization and Testing in a Human Tumor Xenograft Model", Cancer Research, vol. 60, Mar. 2000, pp. 1197-1201.
D'Arrigo, Paola et al "Discrimination of Chain Positions in Mixed Short/Long-Chain Glycerophosphocholines by NMR Chemical Shift Variations", Journal of American Oil Chemical Society, vol. 85, 2008, pp. 1005-1011.
Hauck, Marlene L. et al "Phase I Trial of Doxorubicin-Containing low Temperature Sensitive Liposomes in Spontaneous Canine Tumors", Cancer Theraphy: Clinical Cancer Res. vol. 12, No. 13, 2006, pp. 4004-4010.
Kong, Garheng et al "Efficacy of Liposomes and Hyperthermia in a Human Tumor Xenograft Model: Importance of Triggered Drug Release" Cancer Research, vol. 60, Dec. 2000, pp. 6950-6957.
Langereis, Sander et al "A Temperature-Sensitive Liposomal H CEST and F Contrast Agent for MR Image-Guided Drug Delivery", Journal of the America Chemical Society, 2009, vol. 131, pp. 1380-1381.

(Continued)

Primary Examiner — Michael G Hartley
Assistant Examiner — Jennifer Lamberski

(57) ABSTRACT

Disclosed are carriers for drugs and/or MR imaging agents having a lipid bilayer shell comprising a phospholipid having two terminal alkyl chains, one being a short chain having a chain length of at most seven carbon atoms, the other being a long chain having a chain length of at least fifteen carbon atoms. The mixed long/short chain phospholipids serve to tune the release properties of the carrier. Preferred phospholipids are phosphatidylcholines.

17 Claims, 7 Drawing Sheets

(56) References Cited

OTHER PUBLICATIONS

Tokumura, Akira et al "Mass Spectrometric Analyses of Biologically Active Choline Phospholipids and Their Lyso Derivatives", Chemical & Pharmaceutical Bulletin, vol. 31, No. 12, pp. 4425-4435. 1983.
Yatvin, M.B. et al "Design of Liposomes for Enhanced Local Release of Drugs by Hyperthermia", Science, vol. 202, 1978, pp. 1290-1293.
Terreno, Enzo et al "Highly Shifted LIPOCEST Agents based on the Encapsulation of Neutral Polynuclear Paramagnetic Shift Reagents", Chem Communication, 2008, pp. 600-602.
Terreno, Enzo et al "From Spherical to Osmotically Shrunken Paramagnetic Liposomes: An Improved Generation of LIPOCEST MRI Agents with Highly Shifted Water Protons", Magnetic Resonance Imaging, Angew. Chem. Int. Ed, vol. 47, 2007, pp. 966-968.
Aime, Silvio et al "Highly Sensitive MRI Chemical Exchange Saturation Transfer Agents using Liposomes", Angewandte Chemie Int. Ed. vol. 44, 2005, pp. 5513-5515.
Aime, Silvio et al "Gd-Loaded Liposomes as T1, Susceptibility, and CEST Agents, All in One", JACS Communications, vol. 129, 2007, pp. 2430-2431.
Peters, J.A. et al "Lanthanide Induced Shifts and Relaxation Rate Enhancements", Progress in Nuclear Magnetic Resonance Spectroscopy, vol. 28, 1996, pp. 283-350.
Caravan, Peter et al Gadolinium(III) Chelates as MRI Contrast Agents: Structure, Dynamics, and Applications, Chemical Rev. vol. 99, 1999, pp. 2293-2352.
Torchilin, Vladimir P. et al "Characterization of Liposomes" Liposomes Second Edition, Practical Approach, Oxford Press, 1990, pp. 33-104.

\* cited by examiner

LIPID BILAYER CARRIER FOR DRUGS OR IMAGING AGENTS

FIELD OF THE INVENTION

The invention pertains to carriers comprising a lipid bilayer shell enclosing a cavity, notably liposomes, and to the use thereof for releasing drugs or as an imaging agent. Particularly, the invention pertains to carriers such as liposomes, suitable for the temperature-responsive release of materials contained therein, and to the localized delivery of drugs and/or imaging agents by means of temperature-responsive release carriers.

BACKGROUND OF THE INVENTION

Many diseases that are mostly localized in a certain tissue are treated with systemically administered drugs. A well-known example of standard cancer therapy is a systemic chemotherapy coming along with significant side effects for the patient due to undesired biodistribution and toxicity. The therapeutic window of these drugs is usually defined by the minimal required therapeutic concentration in the diseased tissue on the one hand, and the toxic effects in non-targeted organs, e.g. liver, spleen, on the other.

Localized treatment by, for example, local release of cytostatics from nanocarriers promises a more efficient treatment and a larger therapeutic window compared to standard therapeutics. Localized drug delivery is also important if other therapeutic options such as surgery are too risky as is often the case for liver cancers. Localized drug delivery can also become the preferred treatment option for many indications in cardiovascular disease (CVD), such as atherosclerosis in the coronary arteries.

Medical imaging technology, such as magnetic resonance imaging (MRI) or ultrasound imaging, can not only be used for treatment planning, but also to control local drug delivery under image guidance. Focused ultrasound is the method of choice to induce local drug delivery, since it offers several advantages. This technique is non-invasive, can be focused on the diseased tissue and shows only very limited adverse effects on the surrounding tissue. Ultrasound can provide two kinds of trigger for drug delivery. First, the target tissue can be heated in a controlled way with a precision of about half a degree centigrade in a temperature range from body temperature up to 100° C. Second, the ultrasound waves are strong pressure oscillations that provide a stimulus for drug delivery based on mechanical forces.

The skilled person faces several challenges in providing carrier systems for the release of materials such as drugs or imaging compounds. Thus, e.g., the carrier system needs to be designed such that it can be loaded with a sufficient amount of said materials. Particularly if the material to be released comprises drugs, the carrier system should be sensitive to an external stimulus, such as (local) changes in temperature or pressure which allow for quick and localized release of a drug. Moreover, the drug delivery process needs to be under full control, i.e. the drug release at the site of treatment must be measurable in vivo, the amount and rate of drug release should serve as an input parameter for the determination of the subsequent stimulus application, hence drug delivery could be controlled in an image-guided feedback loop.

A significant improvement in the efficacy of liposomal drug therapies can be obtained by triggering the release of drugs by means of an external stimulus. One approach to trigger the release of encapsulated molecules is the use of temperature-sensitive liposomes. In this case, the release of the drug occurs above the melting phase transition temperature (Tm) of the liposome membrane. At Tm, structural changes in the lipid membrane occur as it transfers from a gel-like to the liquid state phase. This transition leads to a distinct increase in the permeability of the membrane for solutes and water. The incorporation of phosphatidylcholines, such as lyso-PC, acetylated MPPC, and platelet activation factor (PAF), in the bilayer of liposomes has a pronounced effect on the properties of the liposomes. In 1988, Bratton et al. demonstrated that these lipids can be utilized to decrease the Tm of dipalmitoylphosphatidylcholine (DPPC)-based liposomes. Needham et al. have designed low temperature-sensitive liposomes (LTSLs) composed of lyso-PC/DPPC/DPPE-PEG2000 that release encapsulated doxorubicin (ThermoDox®) in a matter of seconds in response to mild hyperthermic conditions (39-42° C.). DPPC is dipalmitoylphosphatidylcholine, PEG2000 is polyethylene glycol of an average molecular weight of about 2000 Daltons. The quick release of aqueous solutes from the interior of these temperature-sensitive systems at temperatures close to the Tm was ascribed to the formation of transient pores. These pores are thermodynamically stable in the presence of micelle-forming phospholipids, such as lyso-PC and PEGylated phospholipids. Moreover, the transient pore formation has been ascribed to the accumulation of lyso lipids by lateral diffusion within the lipid bilayer. Preclinical experiments with lyso-PC based LTSLs loaded with doxorubicin in combination with an externally applied regional temperature increase clearly showed an improved efficacy of temperature-induced drug delivery. Instead of relying on liposomal accumulation in the tumor, hyperthermia was applied during the first hour after injection of the temperature-sensitive liposomal formulation of doxorubicin. This cytostatic drug was rapidly released in the microvasculature of the tumor and subsequently taken up by the tumor cells. Although lyso-PC based LTSLs loaded with doxorubicin have been successfully applied for drug delivery in combination with needle-based RF ablation, the stability of the liposomal formulation in plasma at 37° C. is suboptimal, showing up to 40% release of doxorubicin in 1 hour.

EP 331 504 discloses thermosensitive liposomes made from phospho lipids that carry two aliphatic groups that can be slightly with respect to the length of the aliphatic tail, e.g. one having at least 8 carbon atoms and the other having at least 10 carbon atoms. Preferably, both aliphatic groups have 12-18 carbon atoms. This reference reflects an early attempt, of more than two decades ago, and has not proven to provide thermosensitive liposomes that meet the current demands for use in modern imaging and therapy applications. These demands relate to providing improved temperature transition per se, as well as to, e.g., providing a better contrast enhancement in MRI-based drug delivery, and properties such as improved water exchange ratio's over the lipid shell. The latter is important for MR imaging, wherein it is desired to have a strong contrast enhancement between the intact carrier and the released MR contrast agent. This contrast enhancement is high in the event of a relatively low transmembrane water exchange rate.

Thus, it is desired that carrier systems for the localized delivery of drugs can be optimized with a view to application in MRI-based drug delivery. Particularly, it is desired to provide carriers that enable achieving a better contrast enhancement in these applications.

SUMMARY OF THE INVENTION

In order to better address the aforementioned desires, the invention, in one aspect, presents a thermosensitive carrier comprising a lipid bilayer shell, wherein the lipid bilayer comprises a phospho lipid having two terminal alkyl chains, one being a short chain having a chain length of at most seven carbon atoms, the other being a long chain having a chain length of at least fifteen carbon atoms.

In another aspect, the invention provides the use of a phospho lipid having two terminal alkyl chains, one being a short chain having a chain length of at most seven carbon atoms, the other being a long chain having a chain length of at least fifteen carbon atoms, as a component of thermosensitive carriers, particularly liposomes.

In yet another aspect, the invention resides in a system comprising a drug substance and a thermosensitive carrier for said drug substance, wherein the carrier comprises a lipid bilayer that encloses a cavity comprising the drug substance, wherein said lipid bilayer comprises a phospho lipid having two terminal alkyl chains, one being a short chain having a chain length of at most seven carbon atoms, the other being a long chain having a chain length of at least fifteen carbon atoms.

In a further aspect, the invention resides in a system comprising an MRI contrast enhancing substance and a carrier comprising a semipermeable lipid bilayer that encloses a cavity comprising water, wherein said lipid bilayer comprises a phospho lipid having two terminal alkyl chains, one being a short chain having a chain length of at most seven carbon atoms, the other being a long chain having a chain length of at least fifteen carbon atoms.

In a still further aspect, the invention relates to any of the foregoing carriers for use in the in vivo release of a substance contained therein, respectively to treatment and imaging methods comprising administering any of the foregoing carriers to an animal, preferably a human, and affecting the in vivo release of a substance contained therein.

DETAILED DESCRIPTION OF THE INVENTION

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention relates to carriers comprising a lipid bilayer shell. Particularly, such shells enclose a cavity, and are semipermeable, typically comprising phospholipids. The carriers include microcarriers, having a particle size of the order of a diameter of several to tens of microns, and nanocarriers, having a particle size of the order of tens to hundredths of nanometers. In the context of the invention, the carriers are hereinafter referred to as liposomes.

Liposomes are generally spherical vesicles comprising a bilayer membrane enclosing a cavity (the lumen). The bilayer can be made up of at least one phospho lipid and may or may not comprise cholesterol. Liposomes can be composed of naturally-derived phospholipids with mixed lipid chains (like egg phosphatidylethanolamine), or of pure surfactant components like dioleoylphosphatidyletha-nolamine (DOPE). The term liposomes, as used in the description of the invention, includes lipid spheres usually denoted micelles.

A typical example of a semipermeable shell is also found in semipermeable membranes comprising a phospho lipid bilayer. A phospho lipid bilayer is the most permeable to small, uncharged solutes. Liposomes can be made on the basis of a phospho lipid bilayer. In a broad sense, the invention is based on the selection of mixed short chain/long chain phospho lipids as a component for the lipid bilayer of liposomes. Short is meant here in the sense of having at most seven carbon atoms, and long is meant here in the sense of having a chain length of at least fifteen carbon atoms. By thus providing two terminal alkyl chains of tunable length, and by specifying that one of these chains must be short and the other must be long, the inventors believe (without wishing to be bound by theory) that this accounts for several unexpected beneficial effects.

Thus, the mixed short/long chain phospholipids allow tuning the properties of the shell of the carrier that relate to drug release. As a result, the carriers of the invention contribute to obtaining a rapid drug release at a predetermined temperature. Also, the invention provides a possibility to tune the water exchange ratio across the shell of the carrier, which can be utilized to maximize the MR contrast enhancement between body temperature and hyperthermia. The latter is important in the field of MR image-guided drug delivery by means drug release affected by a temperature-response.

Mixed Short/Long Chain Phospholipids

In a broad fashion, the invention is applicable to any phospholipids that can be incorporated into the lipid bilayer of a liposome. The main requirement is that a short and a long alkyl chain are present. Conceivably, the long alkyl chain comprises a double bond, but saturated chains are preferred. According to the invention, the lengths of these chains can be varied in order to tune the lipid bilayer properties.

It will be understood that the terms "short" and "long" in their most general sense are relative. I.e., if the short chain has two carbon atoms, a chain having more than six carbon atoms could be considered long. On the other hand, if the long chain has fifteen carbon atoms, a chain having ten carbon atoms could be considered short. In general, the difference in length between the short chain and the long chain will be at least ten carbon atoms, preferably between eleven and sixteen carbon atoms.

The short chain preferably has a length of length of at most five carbon atoms. In more preferred embodiments, the short chain has a length of two, three, or four carbon atoms. The long chain preferably has a chain length of at least fifteen carbon atoms. The upper limit for the long chain preferably is thirty carbon atoms, more preferably twenty carbon atoms. In preferred embodiments the long chain has fifteen, sixteen, seventeen, or eighteen carbon atoms.

Phospholipids are known and generally refer to phosphatidylcholine, phosphatidyl-ethanolamine, phosphatidylserine and phosphatidylinositol. In the invention it is preferred to employ phosphatidylcholine.

In a further preferred embodiment, the mixed short chain/long chain phospholipids satisfy either of the following formula (I) or (II).

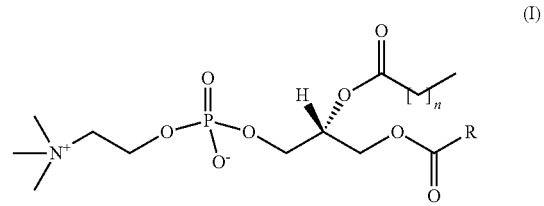

(I)

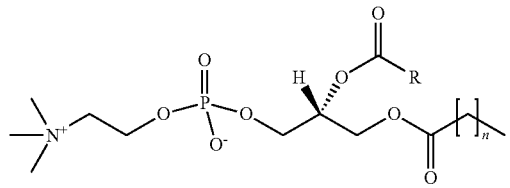

(II)

Herein R is an alkyl chain of fifteen to thirty carbon atoms, and is preferably $C_{15}H_{31}$ or $C_{17}H_{35}$; n is an integer of 1 to 6, preferably 1 to 4, and more preferably 2-3.

These compounds can be synthesized by esterification of lyso-PC with the corresponding anhydrides. An exemplified reaction scheme is given in Scheme 1 below:

Scheme 1

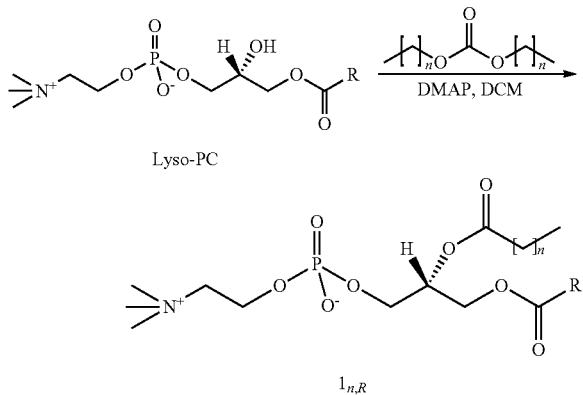

Herein DMAP stands for 4-dimethyl amino pyridine and DCM stands for dichloro methane. The indication $1_{n,R}$ refers to the compound of formula (I) above.

In another aspect, the invention relates to the use of any of the mixed short chain/long chain phospholipids as described above, as a component of thermosensitive liposomes, particularly for the purpose of tuning the release properties of the liposomes.

Thermosensitive Carriers

The invention concerns carriers that are thermosensitive. This means that the physical or chemical state of the carrier is dependent on its temperature.

Any thermosensitive carrier that can package a molecule of interest and that is intact at body temperature (i.e. 37° C.) but destroyed at any other, non-body temperature that can be tolerated by a subject, may be used. Carriers of the invention include but are not limited to thermosensitive micro- and nanoparticles, thermosensitive liposomes, thermosensitive nanovesicles and thermosensitive nanospheres.

It will be appreciated by the skilled person that the thermosensitive nature of a carrier should be understood in the context of in vivo administration, preferably human subjects. I.e., the temperatures at which structural changes will occur in the carrier so as to release it contents (e.g. by opening up the lipid bilayer of a thermosensitive liposome) are generally within a level that can be tolerated by a subject, i.e. normally below 50° C., and preferably 1-5 degrees above body-temperature.

Thermosensitive carriers for use in the invention ideally retain their structure at about 37° C., i.e. human body temperature, but are destroyed at a higher temperature, preferably only slightly elevated above human body temperature, and preferably also above pyrexic body temperature. Typically about 42° C. (mild hyperthermia) is a highly useful temperature for thermally induced (local) drug delivery. Heat can be applied in any physiologically acceptable way, preferably by using a focused energy source capable of inducing highly localized hyperthermia. The energy can be provided through, e.g., microwaves, ultrasound, magnetic induction, infrared or light energy.

Thermosensitive nanovesicles generally have a diameter of up to 100 nm. In the context of this invention, vesicles larger than 100 nm, typically up to 5000 nm, are considered as microvesicles. The word vesicle describes any type of micro- or nanovesicle. Vesicles, such as liposomal vesicles, typically include a cavity which may contain any substance of interest. In the invention this is preferred, as outlined above.

Thermosensitive liposomes include but are not limited to any liposome, including those having a prolonged half-life, e.g. PEGylated liposomes.

Thermosensitive liposomes are known in the art. Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic, D. D., Liposomes from physics to applications, Elsevier Science Publishers, Amsterdam, 1993; Liposomes, Marcel Dekker, Inc., New York (1983).

Entrapment of a drug or other substance within liposomes of the present invention may also be carried out using any conventional method in the art. In preparing liposome compositions of the present invention, stabilizers such as antioxidants and other additives may be used as long as they do not interfere substantially with the purpose of the invention.

The shell will generally be semipermeable. The term "semipermeable" is well understood in the art. In general it refers to the property of a membrane, such as a shell, to be selectively permeable, sometimes also denoted partially or differentially permeable. A shell in this sense indicates a structure that basically is closed in the sense that it is a not fully open wall, and preferably a mostly closed wall, (in this case a shell enclosing a cavity), that allows certain molecules or ions to pass through it by diffusion.

In this description, the semipermeability of the shell generally refers to its ability to allow the MR analyte to pass through it by diffusion. Hence, if the combination of analyte (such as water, or other small molecules comprising protons) and shell (such as a lipid bilayer) is such that the analyte is capable of passing through the shell by diffusion, the shell is considered semipermeable.

References on thermosensitive carriers having a semipermeable shell, are e.g. U.S. Pat. No. 6,726,925, US 2006/0057192, US 2007/0077230A1 and JP 2006-306794.

In another aspect, the invention resides in a drug delivery system comprising a carrier according to any of the embodiments as described above, and at least one drug substance.

In a further aspect, the invention resides in an imaging system comprising a carrier according to any of the embodiments as described above, and at least one MRI contrast enhancing substance.

In yet another aspect, the invention relates to a system comprising a carrier according to any of the embodiments as described above, a drug substance, and an MRI contrast enhancing substance.

In a still further aspect, the invention presents a combined system for imaged drug delivery, comprising a carrier according to any of the embodiments as described above, at least one drug substance, and at least one MRI contrast enhancing substance.

In another aspect, the invention relates to any of the foregoing carriers for use in the in vivo release of a substance contained therein, respectively to treatment and imaging methods comprising administering any of the foregoing carriers to an animal, preferably a human, and affecting the in vivo release of a substance contained therein.

In yet another aspect, the invention provides a method for the MRI guided delivery of a drug to a subject, comprising the administration to said subject of a carrier according to any one of the embodiments described above provided with the drug and with an MRI contrast enhancing substance, allowing the carrier to release the drug and the MRI contrast enhancing substance, and rendering an MR image using the contrast provided by the contrast enhancing substance.

Drug Carriers

In one aspect, the invention relates to a carrier suitable for the localized delivery of a biologically active agent, such as a drug. Hereinafter, the term "biologically active agent" will be referred to, in short, as "drug" and the carrier as a "drug carrier." A drug carrier in the context of the present invention refers to any material in or on which a bio-active agent can be contained so as to be capable of being released in the body of a subject.

The drug carrier is to be introduced into the body of a person to be subjected to MRI. This will be e.g. by injection in the blood stream, or by other methods to introduce the carrier into body fluid.

A drug is a chemical substance used in the treatment, cure, prevention, or diagnosis of a disease or disorder, or used to otherwise enhance physical or mental well-being. The guided delivery foreseen with the present invention will mostly be useful therapeutic agents (i.e. drugs in a strict sense, intended for therapy or prevention of diseases or disorders), but also for agents that are administered for diagnostic purposes. Although other bio-active agents, i.e. those that are not therapeutic or diagnostic, such as functional food ingredients, will not generally be subjected to guided and/or monitored delivery, such could be done using the present invention if desired.

The most optimal use of the invention is attained in the case of targeted therapeutics, i.e. drugs that are intended for targeted delivery, as such delivery will by nature benefit most from the monitoring made available by the invention. This pertains, e.g., to agents in the treatment of tumors to be delivered on site, to agents in the treatment or prevention of cardiovascular disorders, such as atherosclerosis in the coronary arteries, or to antithrombotic agents (e.g. for locally resolving blood cloths) or agents that require passing the blood-brain barrier such as neuromodulators as can be used in the treatment of neural conditions such as epilepsy, Alzheimer's disease, Parkinson's disease, or stroke. Benefits from the guidance and monitoring of targeted drug delivery are also applicable to targeted diagnostic agents. Similarly as with targeted therapeutics, here too cancer is an area where site-specific delivery can be of importance.

Bio-active agents suitable for use in the present invention include biologically active agents including therapeutic drugs, endogenous molecules, and pharmacologically active agents, including antibodies; nutritional molecules; cosmetic agents; diagnostic agents; and additional contrast agents for imaging. As used herein, an active agent includes pharmacologically acceptable salts of active agents.

The drug carriers of the present invention can comprise either hydrophilic or hydrophobic bioactive agents. A hydrophilic bioactive agent could be encapsulated in the aqueous compartment of the carrier, whereas hydrophobic bioactive agents could be incorporated in hydrophobic domains of the carrier, for instance in the lipid bilayer of liposomes. Nucleic acids, carbohydrates and, in general, proteins and peptides are water soluble or hydrophilic. For instance, bioactive agents which are small molecules, lipids, lipopolysaccharides, polynucleotides and antisense nucleotides (gene therapy agents) are also envisaged. Such biologically active agents, which may be incorporated, thus include non-peptide, non-protein drugs. It is possible within the scope of the present invention to incorporate drugs of a polymeric nature, but also to incorporate drugs of a relatively small molecular weight of less than 1500 g/mol, or even less than 500 g/mol.

Accordingly, compounds envisaged for use as bioactive agents in the context of the present invention include any compound with therapeutic or prophylactic effects. It can be a compound that affects or participates in tissue growth, cell growth, cell differentiation, a compound that is able to invoke a biological action such as an immune response, or a compound that can play any other role in one or more biological processes. A non-limiting list of examples includes antimicrobial agents (including antibacterial, antiviral agents and anti-fungal agents), anti-viral agents, anti-tumor agents, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, anti metabolites, antiproliferatives (including antiangiogenesis agents), anticancer chemotherapeutic agents, anti-inflammatory steroid or nonsteroidal anti-inflammatory agents, immunosuppressive agents, growth hormone antagonists, growth factors, dopamine agonists, radiotherapeutic agents, extracellular matrix components, ACE inhibitors, free radical scavengers, chelators, antioxidants, anti polymerases, and photodynamic therapy agents.

Relatively small peptides may be referred to by the number of amino acids (e.g. di-, tri-, tetrapeptides). A peptide with a relatively small number of amide bonds may also be called an oligopeptide (up to 50 amino acids), whereas a peptide with a relatively high number (more than 50 amino acids) may be called a polypeptide or protein. In addition to being a polymer of amino acid residues, certain proteins may further be characterized by the so called quaternary structure, a conglomerate of a number of polypeptides that are not necessarily chemically linked by amide bonds but are bonded by forces generally known to the skilled professional, such as electrostatic forces and Vanderwaals forces. The term peptides, proteins or mixtures thereof as used herein is to include all above mentioned possibilities.

Other examples of peptides or proteins or entities comprising peptides or proteins, which may advantageously be contained in the carrier include, but are not limited to, immunogenic peptides or immunogenic proteins, which include, but are not limited to, the following:

Toxins such as diphtheria toxin and tetanus toxin.

Viral surface antigens or parts of viruses such as adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses and Yellow Fever Virus. Bacterial surface antigens or parts of bacteria such as *Bordetella pertussis, Helicobacter pylori, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera* and *Yersinia pestis*. Surface antigens of parasites causing disease or portions of parasites such as *Plasmodium vivax* (malaria), *Plasmodium falciparum* (malaria), *Plasmodium ovale* (malaria), *Plasmodium malariae* (malaria), *Leishmania tropica* (leishmaniasis), *Leishmania donovani*), leishmaniasis), *Leishmania branziliensis* (leishmaniasis), *Trypanosoma rhodescense* (sleeping sickness), *Trypanosoma gambiense* (sleeping sickness), *Trypanosoma cruzi* (Chagas' disease), *Schistosoma mansoni* (schistosomiasis), *Schistosomoma haematobium* (schistomiasis), *Schistosoma japonicum* (shichtomiasis), *Trichinella spiralis* (trichinosis), *Stronglyloides duodenale* (hookworm), *Ancyclostoma duodenale* (hookworm), *Necator americanus* (hookworm), *Wucheria bancrofti* (filariasis), *Brugia malaya* (filariasis), *Loa loa* (filariasis), *Dipetalonema perstaris* (filariasis), *Dracuncula medinensis* (filariasis), and *Onchocerca volvulus* (filariasis).

Immunoglobulins such as IgG, IgA, IgM, Antirabies immunoglobulin, and Antivaccinia immunoglobulin.

Antitoxin such as Botulinum antitoxin, diphtheria antitoxin, gas gangrene antitoxin, tetanus antitoxin.

Antigens which elicit an immune response against foot and mouth disease.

Hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.

Examples of other proteins or peptides are albumin, atrial natriuretic factor, renin, superoxide dismutase, alpha 1-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-alpha-endorphin, gonadotropin releasing hormone, leuprolide, alpha-MSH and metkephamid.

Anti-tumor agents such as altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin and paclitaxel.

Antimicrobial agents comprising:

Antibiotics such as ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, and cephalexin. Aminoglycosides such as amikacin, neomycin, dibekacyn, kanamycin, gentamycin, netilmycin, tobramycin. Macrolides such as amphotericin B, novobiocin, bacitracin, nystatin, clindamycin, polymyxins, colistin, rovamycin, erythromycin, spectinomycin, lincomycin, vancomycin Tetracyclines such as chlortetracycline, oxytetracycline, demeclocycline, rolitetracycline, doxycycline, tetracycline and minocycline. Other antibiotics such as chloramphenicol, rifamycin, rifampicin and thiamphenicol.

Chemotherapeutic agents such as the sulfonamides sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole and trimethoprim with sulfamethoxazole or sulfametrole.

Urinary tract antiseptics such as methanamine, quinolones (norfloxacin, cinoxacin), nalidixic acid, nitro-compounds (nitrofurantoine, nifurtoinol) and oxolinic acid.

Drug for anaerobic infections such as metronidazole.

Drugs for tuberculosis such as aminosalicyclic acid, isoniazide, cycloserine, rifampicine, ethambutol, tiocarlide, ethionamide and viomycin.

Drugs for leprosy such as amithiozone, rifampicine, clofazimine, sodium sulfoxone and diaminodiphenylsulfone (DDS, dapsone).

Antifungal agents such as amphotericin B, ketoconazole, clotrimazole, miconazole, econazole, natamycin, flucytosine, nystatine and griseofulvin.

Antiviral agents such as aciclovir, idoxuridine, amantidine, methisazone, cytarabine, vidarabine and ganciclovir.

Chemotherapy of amebiasis such as chloroquine, iodoquinol, clioquinol, metronidazole, dehydroemetine, paromomycin, diloxanide, furoatetinidazole and emetine.

Anti-malarial agents such as chloroquine, pyrimethamine, hydroxychloroquine, quinine, mefloquine, sulfadoxine/pyrimethamine, pentamidine, sodium suramin, primaquine, trimethoprim and proguanil.

Anti-helminthiasis agents such as antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole and niclosamide.

Anti-inflammatory agents such as acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen and tolmetin.

Anti-gout agents such as colchicine and allopurinol.

Centrally acting (opoid) analgesics such as alfentanil, methadone, bezitramide, morphine, buprenorfine, nicomorphine, butorfanol, pentazocine, codeine, pethidine, dextromoramide, piritranide, dextropropoxyphene, sufentanil and fentanyl.

Local anesthetics such as articaine, mepivacaine, bupivacaine, prilocaine, etidocaine, procaine, lidocaine and tetracaine.

Drugs for Parkinson's disease such as amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide and trihexyphenidyl.

Centrally active muscle relaxants such as baclofen, carisoprodol, chlormezanone, chlorzoxazone, cyclobenzaprine, dantrolene, diazepam, febarbamate, mefenoxalone, mephenesin, metoxalone, methocarbamol and tolperisone.

Corticosteroids comprising:

Mineralocorticosteroids such as cortisol, desoxycorticosterone and flurohydrocortisone.

Glucocorticosteroids such as beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide).

Androgens comprising:

Androgenic steroids used in therapy such as danazole, fluoxymesterone, mesterolone, methyltestosterone, testosterone and salts thereof.

Anabolic steroids used in therapy such as calusterone, nandro lone and salts thereof, dromostanolone, oxandrolone, ethylestrenol, oxymetho lone, methandriol, stanozolol methandrostenolone and testolactone.

Antiandrogens such as cyproterone acetate.

Estrogens comprising estrogenic steroids used in therapy such as diethylstilbestrol, estradiol, estriol, ethinylestradiol, mestranol and quinestrol.

Anti-estrogens such as chlorotrianisene, clomiphene, ethamoxytriphetol, nafoxidine and tamoxifen.

Progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

Thyroid drugs comprising:

Thyroid drugs used in therapy such as levothyronine and liothyronine

Anti-thyroid drugs used in therapy such as carbimazole, methimazole, methylthiouracil and propylthiouracil.

Apart from bioactive agents which are water soluble, other water-soluble compounds can be incorporated such as anti-oxidants, ions, chelating agents, dyes, imaging compounds.

Preferred therapeutic agents are in the area of cancer (e.g. antitumor) and cardiovascular disease.

Methods of preparing lipophilic drug derivatives which are suitable for nanoparticle or liposome formulation are known in the art (see e.g., U.S. Pat. No. 5,534,499 describing covalent attachment of therapeutic agents to a fatty acid chain of a phospho lipid). Drugs in the present invention can also be prodrugs.

The drug may be present in the inner, the outer, or both of the compartments of the carrier, e.g. in the cavity and/or in the shell of a liposome. The distribution of the drug is independent of the distribution of any other agents comprised in the drug carrier, such as a paramagnetic chemical shift reagent or a paramagnetic agent. A combination of drugs may be used and any of these drugs may be present in the inner, the outer, or both of the compartments of the drug carrier, e.g. in the cavity and/or in the shell of a liposome.

Imaging Agents

In another aspect, the invention relates to carriers that are suitable as imaging agents, preferably for MRI. To this end, the carrier comprises (in the cavity, in the shell, or on the surface thereof) a substance capable of inducing contrast enhancement. These substances include $T_1$ and/or $T_2$ contrast enhancers as well as CEST MRI contrast enhancers.

Almost all current MRI scans are based on the imaging of bulk water molecules, which are present at a very high concentration throughout the whole body in all tissues. If the contrast between different tissues is insufficient to obtain clinical information, MRI contrast agents (CAs), such as low molecular weight complexes of gadolinium, are administered. These paramagnetic complexes reduce the longitudinal ($T_1$) and transverse relaxation times ($T_2$) of the protons of water molecules. Also manganese acts as a $T_1$ contrast agent. The carrier can comprise contrast enhancers for $^1H$ MRI, for $^{19}F$ MRI, or both. In the invention also an all-in-one concept can be realized of $^{19}F$ MRI in combination with $T_1$, $T_2$, and preferably also with CEST contrast, in $^1H$ MRI.

CEST MRI

The invention, in a preferred embodiment, also relates to CEST MRI contrast enhancement. This method serves to generate image contrast by utilizing Chemical Exchange-dependent Saturation Transfer (CEST) from selected, magnetically pre-saturated protons to the bulk water molecules determined by MRI.

If used in CEST MRI, preferred carriers of the invention, i.e. the thermosensitive carriers that have a semipermeable shell enclosing a cavity, contribute to an optimal CEST contrast enhancement. For, the advantage of these carriers is that the CEST contrast enhancement can be conducted on the basis of a paramagnetic chemical shift agent contained in the cavity, in interaction with a pool of protons or other MRI analytes also present in the cavity.

Although the invention, in this preferred embodiment, relates to the application of any CEST-type contrast enhancement to thermosensitive drug release, it is preferred to make use of more advanced CEST methods as have become available.

CEST in combination with a paramagnetic chemical shift reagent (ParaCEST) is a method, in which the magnetization of a pool of paramagnetically shifted protons of a CEST contrast agent is selectively saturated by the application of radio frequency (RF) radiation. The transfer of this saturation to bulk water molecules by proton exchange leads to a reduced amount of excitable water protons in the environment of the CEST contrast agent. Thus a decrease of the bulk water signal intensity is observed, which can be used to create a (negative) contrast enhancement in MRI images.

An approach to obtain a high CEST efficiency is based on utilizing the large number of water molecules of a solution containing a paramagnetic shift reagent (e.g. Na[Tm(dotma)(H$_2$O)]), wherein "H$_4$dotma" stands for $\alpha,\alpha',\alpha'',\alpha'''$-tetramethyl-1,4,7,10-tetraacetic acid and dotma represents the respective fourfold deprotonated tetraanionic form of the ligand, to provide a pool of protons that are chemically shifted and that, therefore, can selectively be saturated by an RF pulse. If this system is encapsulated in a carrier, e.g. a liposome, the magnetic saturation can be transferred to the bulk water molecules at the outside of the carriers, which are not chemically shifted (LipoCEST). The amount of magnetization transfer and hence the extent of contrast enhancement are determined by the rate of the diffusion of water through the shell of the carrier, e.g. a phospholipid membrane, as well as by the amount of water within the carrier.

The optimum water exchange rate is directly correlated with the chemical shift difference between the proton pool inside of the carrier and the bulk water outside of the carrier. The paramagnetic shift that is induced on the water molecules inside the liposomes consists of two main contributions: chemical shift resulting from a direct dipolar interaction between the water molecules and the shift reagent ($\delta_{dip}$), and chemical shift caused by a bulk magnetic susceptibility effect ($\delta_{bms}$). The overall paramagnetic shift is the sum of these two contributions:

$$\delta = \delta_{dip} + \delta_{bms} \quad (1)$$

$\delta_{bms}$ is zero for spherical particles, but it can be significant for anisotropic particles. The aspherical particles experience a force in a magnetic field, which causes them to align with the magnetic field lines. In the case of liposomes, this effect is further increased, if they bear paramagnetic molecules associated with the phospho lipid membrane.

A reference on CEST using aspherical liposomes is Terreno, E. et al. *Angew. Chem. Int. Ed.* 46, 966-968 (2007).

In the invention, a paramagnetic shift reagent can be comprised in any manner in or on the carrier. It is preferred to have the shift reagent in sufficient interaction with a pool of protons by comprising both the reagent and the pool in the cavity of the carrier.

The paramagnetic chemical shift reagent or reagents can basically be any paramagnetic agent suitable to render the relatively large number of water molecules of a solution or dispersion in which it is contained, into a pool of protons that are chemically shifted regarding their MR resonance frequency, with respect to the surrounding protons of the bulk water molecules. As the liposomes comprise a shell that fundamentally allows exchange of protons with their direct environment, the saturation caused by a selective RF pulse will be transferred to the environment of the loaded thermosensitive drug carriers. Thus, upon conducting magnetic resonance imaging, the direct environment of the thermosensitive drug carriers will show a decreased signal intensity as compared to other bulk water molecules, and thus allows to detect the direct environment of the contrast agents due to a decreased signal intensity. The paramagnetic chemical shift reagent is to comprise a paramagnetic compound, i.e. any compound having paramagnetic properties. Preferably the paramagnetic compound comprises a paramagnetic metal ions, e.g. metal ions complexed by chelate ligands. Paramagnetic metal ions are known to the skilled person, and do not require elucidation here. E.g., early and late transition metals, explicitly including chromium, manganese, iron, as well as lanthanides, such as gadolinium, europium, dysprosium, holmium, erbium, thulium, ytterbium.

The paramagnetic chemical shift reagent is to comprise a chelating structure capable of strongly binding to the paramagnetic metal and allowing the metal to interact with water, or with another suitable source of protons. With respect to suitable chelating structures, reference is made to P. Caravan et al., *Chem. Rev.*, 99, 2293-2352 (1999). Preferably the water is at least transiently coordinated to the metal of the paramagnetic reagent. With respect to paramagnetic shift mechanisms, reference is made to J. A. Peters et al., *Prog. Nucl. Magn. Reson. Spectr.*, 28, 283-350 (1999).

In one embodiment, the chelating structure itself also comprises exchangeable protons, e.g. hydroxyl, amine, or amide protons. Suitably, the paramagnetic chemical shift reagent comprises a lanthanide ion coordinated with a chelating structure, e.g. macrocylic lanthanide(III) chelates derived from 1,4,7,10-tetraazacyclododecane-1,4,7,10-tetraacetic acid ($H_4$dota), 1,4,7,10-tetraazacyclododecane-$\alpha,\alpha',\alpha'',\alpha'''$-tetramethyl-1,4,7,10-tetraacetic acid ($H_4$dotma), and related ligands that allow for an axially coordinated water molecule in the paramagnetic reagent. In this respect reference is made to Aime et al., *Angew. Chem. Int. Ed.*, 44, 5513-5515 (2005). A number of the same, similar or different chelating units may be combined in a dendrimeric or polymeric structure providing dendritic or polymeric chemical shift reagents. A general advantage of using dendritic or polymeric paramagnetic compounds is that high effective concentrations of the paramagnetic metal complex can be achieved, without increasing the osmolarity of the solution as much as it would be the case when using mononuclear paramagnetic compounds. Here reference is made to E. Terreno, A. Barge, L. Beltrami, G. Cravotto, D. D. Castelli, F. Fedeli, B. Jebasingh, S. Aime, *Chemical Communications*, 2008, 600-602.

Preferably, the paramagnetic chemical shift reagent is water-soluble. Suitable chemical shift reagents are known to the person skilled in the art. The CEST contrast agents do not require any specific chemical shift reagent, as long as the shift reagent and the pool of protons have a sufficient interaction to result in a pool of chemically shifted protons.

Preferably, the paramagnetic shift reagent is a metal complex comprising a metal ion and a ligand that is based on a multidentate chelate ligand. More preferably, the interaction of the chemical shift reagent with the pool of protons is provided in the form of coordination. Thus it is preferred for the metal complex to have at least one coordination site of the metal left open for the coordination of at least one water molecule.

Examples of suitable water-soluble chemical shift reagents are [Ln(hpdo3a)($H_2O$)] (1), [Ln(dota)($H_2O$)]$^-$ (2), [Ln(dotma)($H_2O$)]$^-$ (3), [Ln(dotam)($H_2O$)]$^{3+}$ (4), and [Ln(dtpa)($H_2O$)]$^{2-}$ (5), including derivatives thereof and related compounds, with Ln being a lanthanide ion.

Preferably the paramagnetic chemical shift reagent is a lanthanide complex such as in formulae 1-5 below:

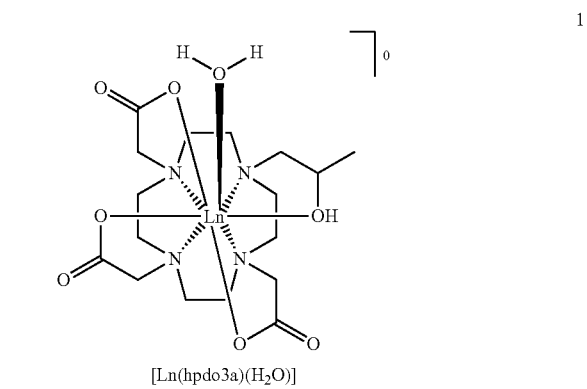

[Ln(hpdo3a)($H_2O$)]

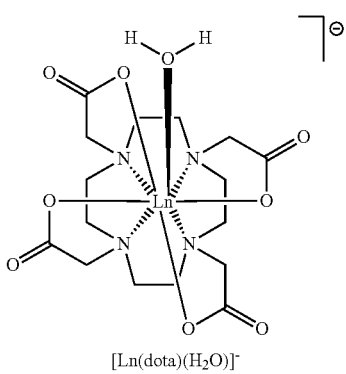

[Ln(dota)(H₂O)]⁻

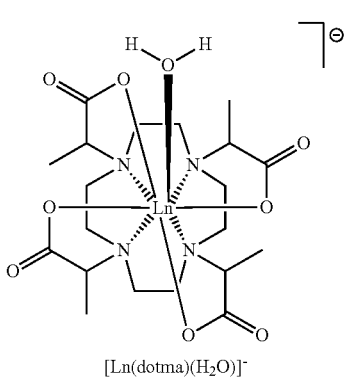

[Ln(dotma)(H₂O)]⁻

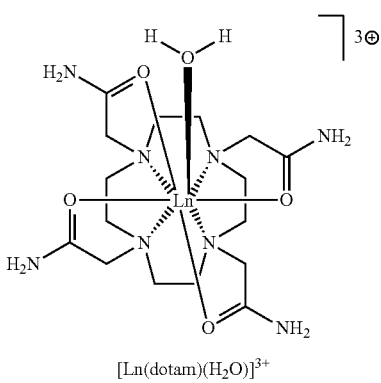

[Ln(dotam)(H₂O)]³⁺

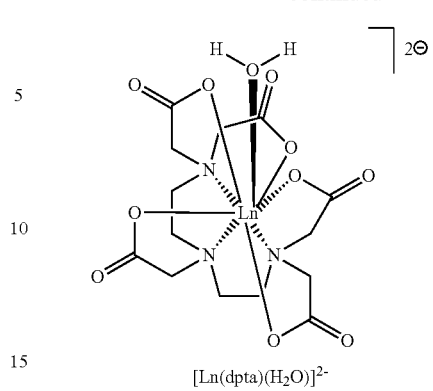

[Ln(dpta)(H₂O)]²⁻ wherein the lanthanide is $Eu^{3+}$, $Dy^{3+}$, $Ho^{3+}$, $Er^{3+}$, $Tm^{3+}$, $Yb^{3+}$, and preferably is $Tm^{3+}$ or $Dy^{3+}$. The paramagnetic chemical shift reagent is typically comprised in the agent in an amount of from 1 mM to 2000 mM, preferably of from 10 mM to 1000 mM, and more preferably of from 50 mM to 200 mM.

The foregoing metal-containing compounds may be dissolved, emulsified, suspended or in any other form distributed homogeneously or inhomogeneously in the cavity, i.e. the inner compartment of the liposome. It may alternatively be linked to the outer compartment of the liposome by at least one covalent or non-covalent bond, or any combination of those. Furthermore the same or at least one different metal-containing compound may be present simultaneously in any of the compartments.

It can be envisaged that the paramagnetic agent and the drug are one and the same, if the drug itself comprises an appropriate metal.

Further Contrast Enhancement Agents

The contrast agents of the invention may comprise $T_1$, $T_2$ or $T_2^*$ reducing agents. In this respect reference is made to Aime et al., *Journal of the American Chemical Society*, 2007, 129, 2430-2431. Also, an all-in-one concept can be realized of $T_1$, $T_2$ or $T_2^*$ and CEST contrast agents.

The chemical shift difference between the internal and the bulk water protons of the thermosensitive drug carriers, can be further enhanced by providing the thermosensitive drug carrier's membrane with a further paramagnetic agent, which is not necessarily a chemical shift reagent. Thus, the orientation of the aspherical carrier in the magnetic field is affected and the aforementioned bulk susceptibility effect is enhanced. The further paramagnetic agent is preferably an amphiphilic compound comprising a lanthanide complex (on the more polar side of the amphiphilic compound), and having an apolar tail which has a tendency to preferably integrate in and align with the lipid bilayer at the thermosensitive drug carrier's surface based on hydrophobic molecular interactions.

These amphiphilic paramagnetic complexes can e.g. be:

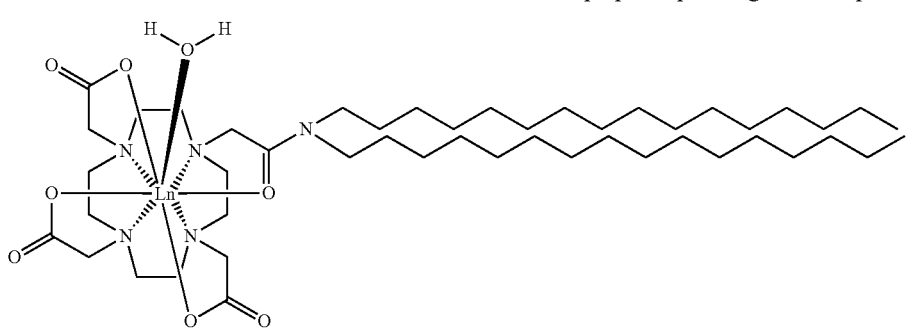

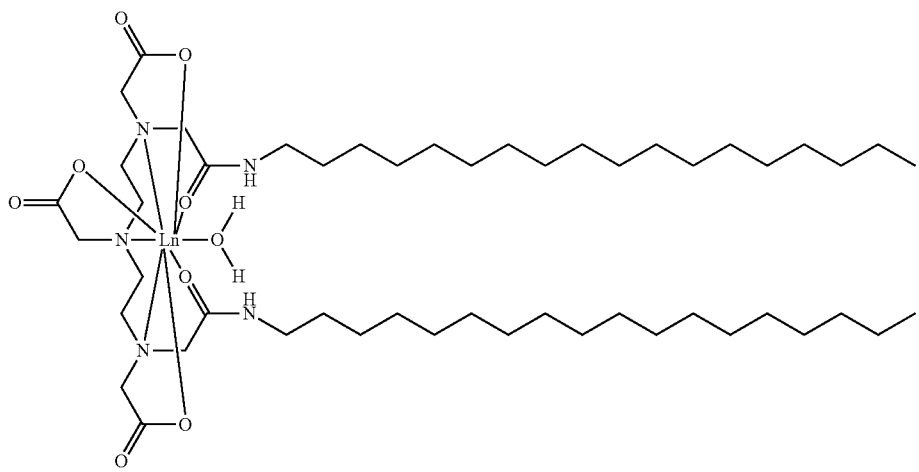
7
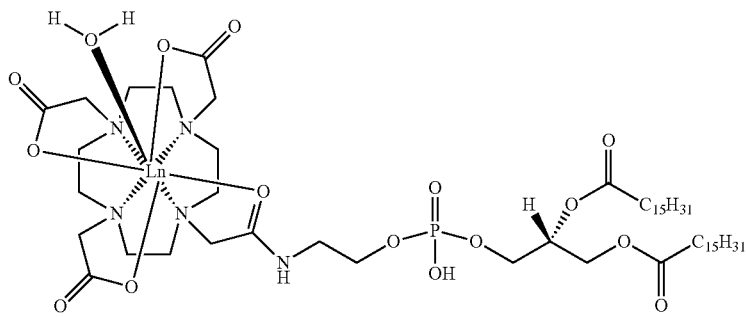
8
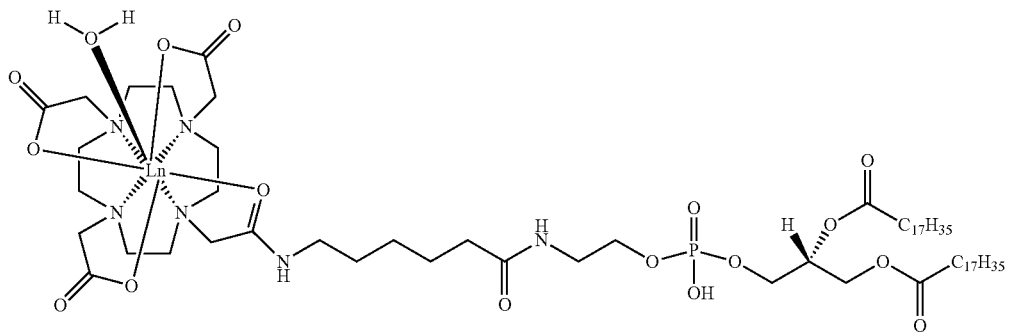
9
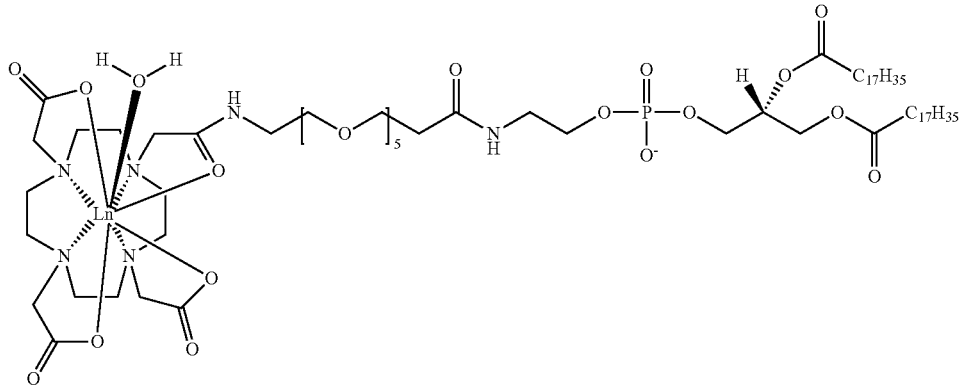
10

Combined $^{19}$F and $^1$H MR Contrast Enhancement

With the invention a suitable combination of $^{19}$F and $^1$H MR can be realized in various ways.

Thus, a dual or multiple-label MR contrast can be generated by utilizing a CEST mechanism and/or $^{19}$F MR. Alternatively, multiple MR contrasts may be generated through the modification of the longitudinal relaxation time ($T_1$), or the transverse relaxation time ($T_2$) of the imaged analyte (typically the protons of water) by a metal-containing compound present in the carrier. Any of these contrast enhancing mechanisms may further be used in any combination thereof.

The dual/multiple labeled MRI contrast, depending on the physical state of the carrier, is monitored either in a subsequent or interleaved manner with conventional MR equipment—or simultaneously, using sequence combinations on dual-tuned spectrometer systems e.g. at $^1$H and $^{19}$F MR resonance frequencies.

In this respect the invention also relates to the use of simultaneous dual nuclei MR imaging in monitoring and/or guiding drug delivery.

The combination of a CEST and a $^{19}$F contrast agent in a thermo-sensitive liposome offers the opportunity to monitor the drug release process independently and simultaneously by means of CEST and $^{19}$F MRI. Simultaneous monitoring of the two different MR signals is mediated by corresponding dual-label MR techniques. This approach leads to several possible advantages. Thus, the spatial distribution of the drug-loaded particles can be assessed prior to drug release by means of CEST MRI; the $^1$H CEST and the $^{19}$F MR signals scale with the amount of released drug, which allows for quantitative control of the delivered drug dose in vivo using a feedback loop; the release of drugs from the carrier at the diseased site can be induced by a local stimulus, such as heating in the case of thermosensitive liposomes using e.g. RF or ultrasound; the CEST MR contrast enhancement can be switched on and off at will.

$^{19}$F MRI Contrast Agents

MR detectable $^{19}$F does not naturally occur in the body, i.e. $^{19}$F MRI will thus be necessarily based on the use of added $^{19}$F contrast agents.

Contrast agents for $^{19}$F MRI preferably have a large number of magnetically equivalent fluoro-groups (the sensitivity scales linearly with the number of magnetically equivalent F atoms per molecule). With a view to the desired combination with CEST MRI, the $^{19}$F MR contrast agents used are preferably water-soluble, and particularly are preferably charged molecules so as to have as high a water-solubility as possible. With a view to application in phospholipid shells, the preferred $^{19}$F contrast agents do not significantly bind, or are not significantly associated with phospholipids. With a view to their release in the human or animal body, the $^{19}$F contrast agents are preferably of low toxicity and high biocompatibility.

Preferred $^{19}$F contrast agents are charged per-F analogs of aliphatic hydrocarbons.

Examples and Drawings

The invention will be illustrated with reference to the following, non-limiting examples and the accompanying non-limiting drawings (FIGS. 1-7).

DESCRIPTION OF THE DRAWINGS

In particular, FIG. 2A depicts the fluorescence and longitudinal relaxivity during a linear temperature increase (0.5 K/min) from 300 K to 323 K for LTSLs containing 10,R (R=C15H31), and FIG. 2B depicts the fluorescence and longitudinal relaxivity during a linear temperature increase (0.5 K/min) from 300 K to 323 K for LTSLs containing 10,R (R=C17H35), in HBS. Meanwhile.

EXAMPLE 1

Figure 1:
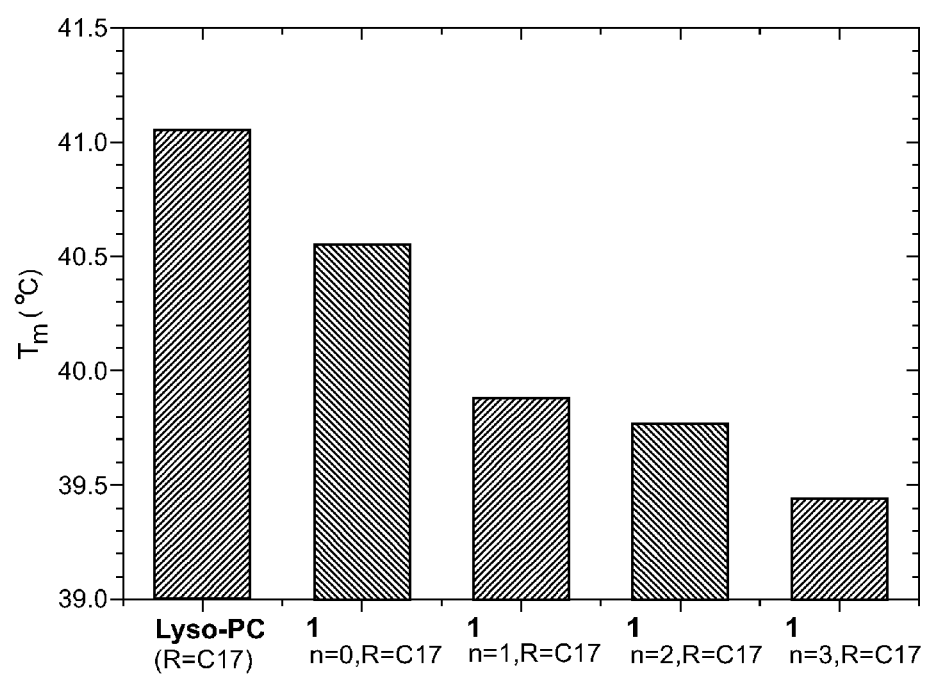
FIG. 1 presents a bar diagram showing the melting phase transition temperatures of temperature sensitive liposomes (TSLs) containing either 10 mol % of Lyso-PC or 10 mol % of $1_{n,R}$ in the lipid bilayer and 250 mM ProHance and doxorubicin in their aqueous lumen.
Figure 2:
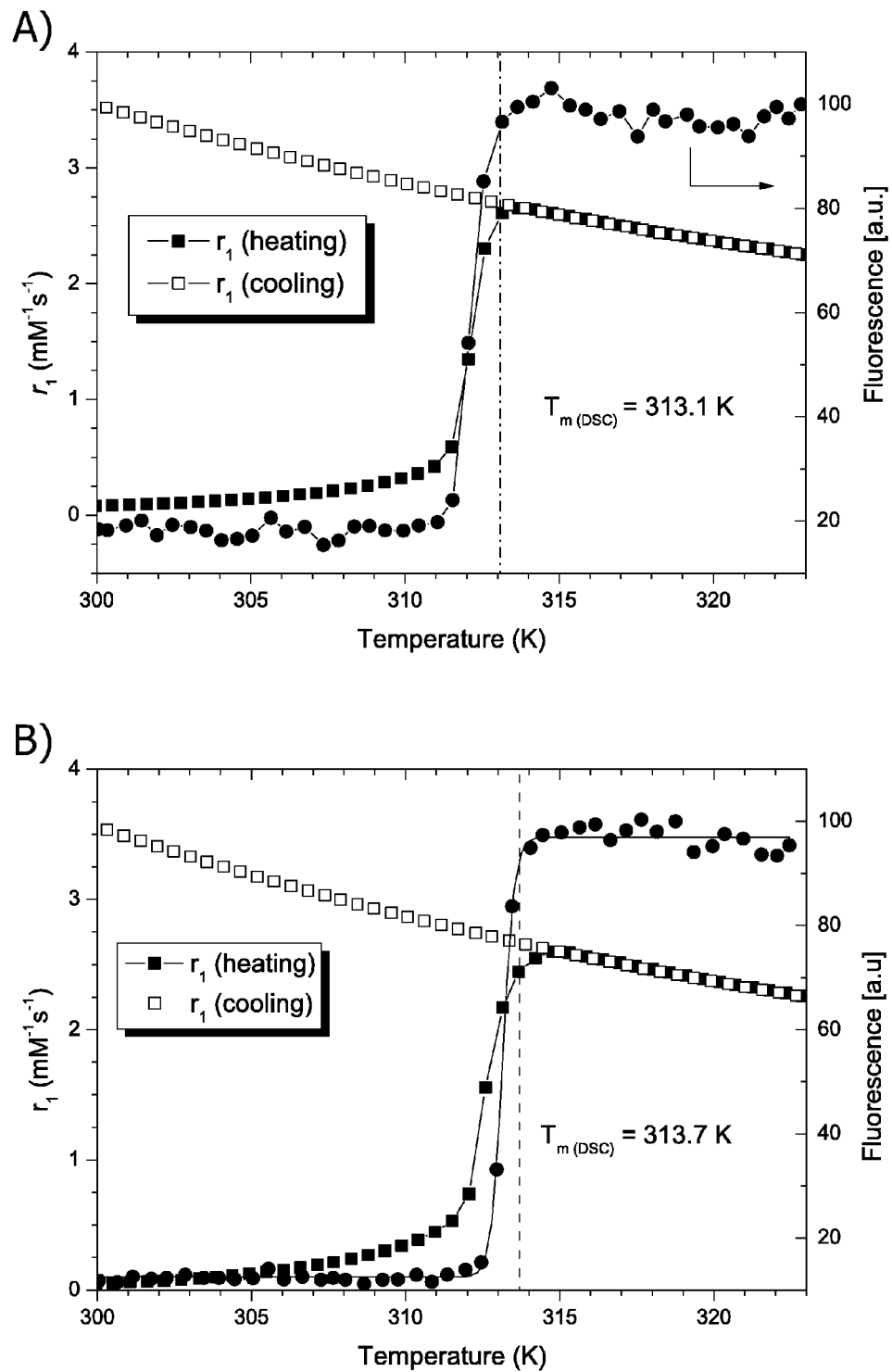
FIGS. 2A and 2B shows fluorescence and longitudinal relaxivity results for TSLs containing 10 mol % acetylated PCs ($1n,R$: n=0, R=C15H31 or C17H35) in the lipid bilayer and 250 mM ProHance and doxorubicin in their aqueous lumen.
FIG. 2C depicts the release of doxorubicin as a function of temperature for LTSLs containing 10,R (R=C15H31)
FIG. 2D depicts the release of doxorubicin as a function of temperature for LTSLs containing 10,R (R=C17H35), in HBS.
Figure 2:
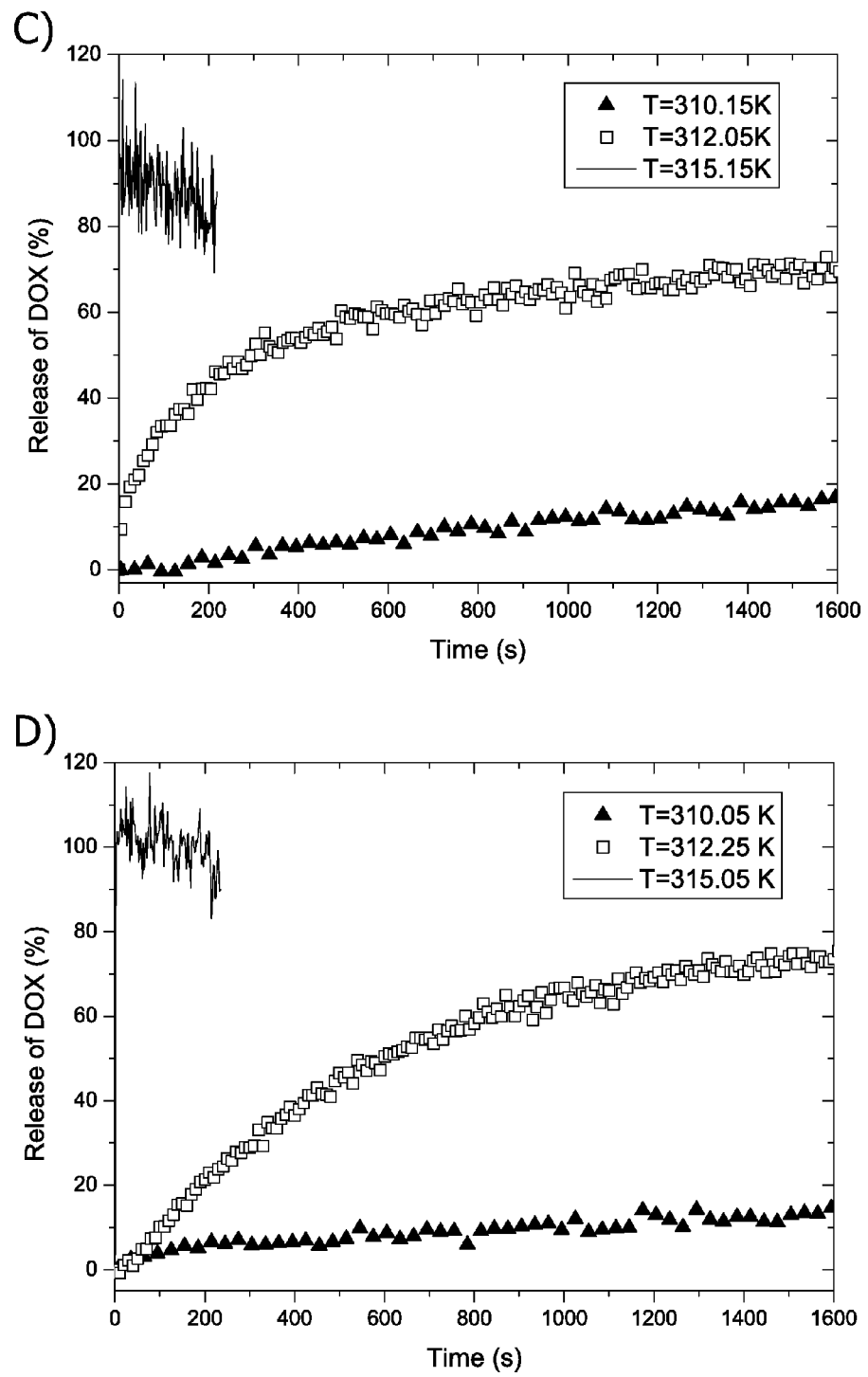
Figure 3:
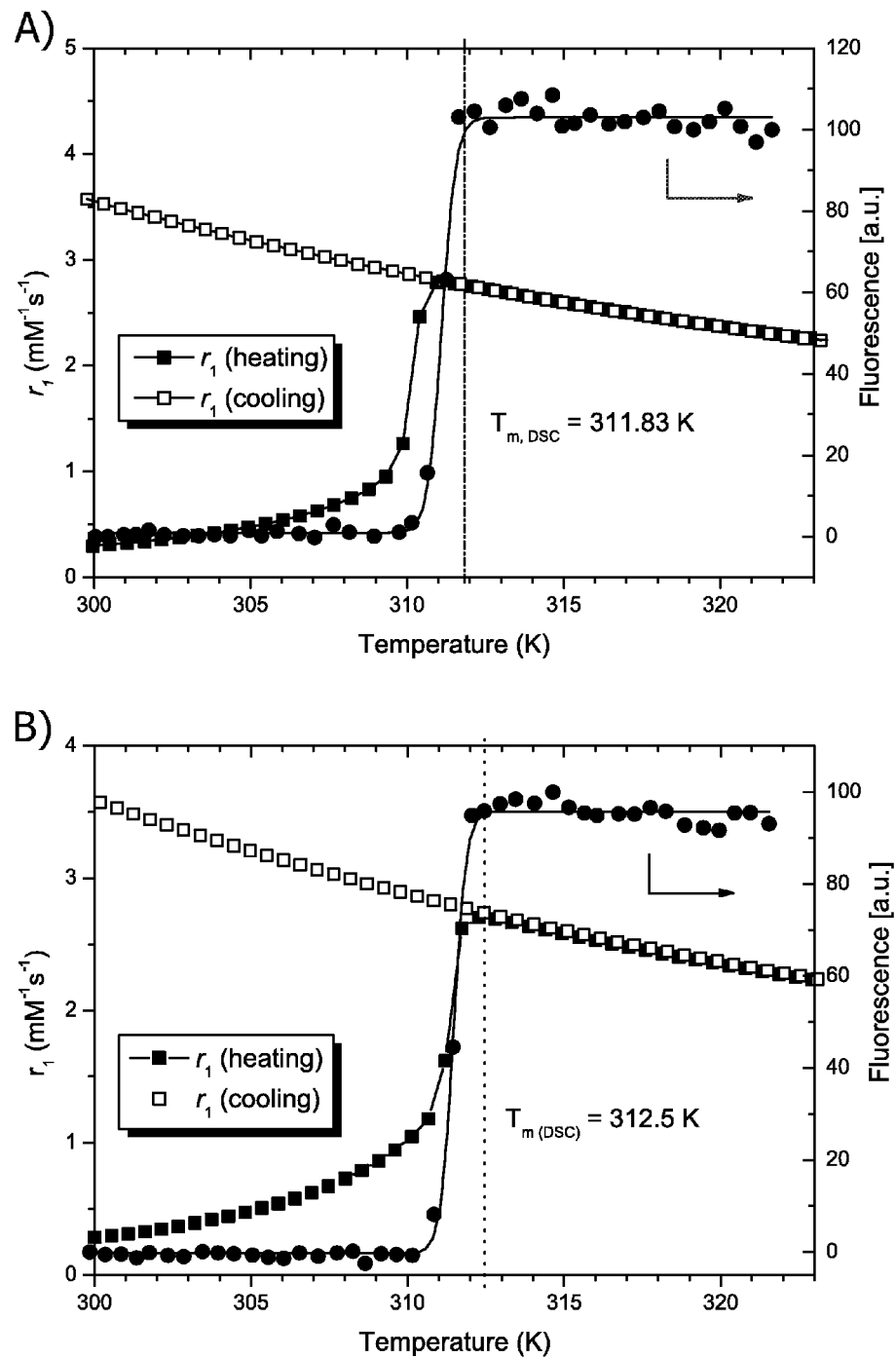
FIG. 3A shows fluorescence and longitudinal relaxivity during a linear temperature increase (0.5 K/min) from 300 K to 323 K for LTSLs containing 13,R (R=C15H31)
FIG. 3B shows fluorescence and longitudinal relaxivity during a linear temperature increase (0.5 K/min) from 300 K to 323 K for LTSLs containing 13,R (R=C17H35), in HBS.
FIG. 3C depicts the release of doxorubicin as a function of temperature for LTSLs containing 13,R (R=C15H31)
FIG. 3D depicts the release of doxorubicin as a function of temperature for LTSLs containing 13,R (R=C17H35), in HBS.
Figure 3:
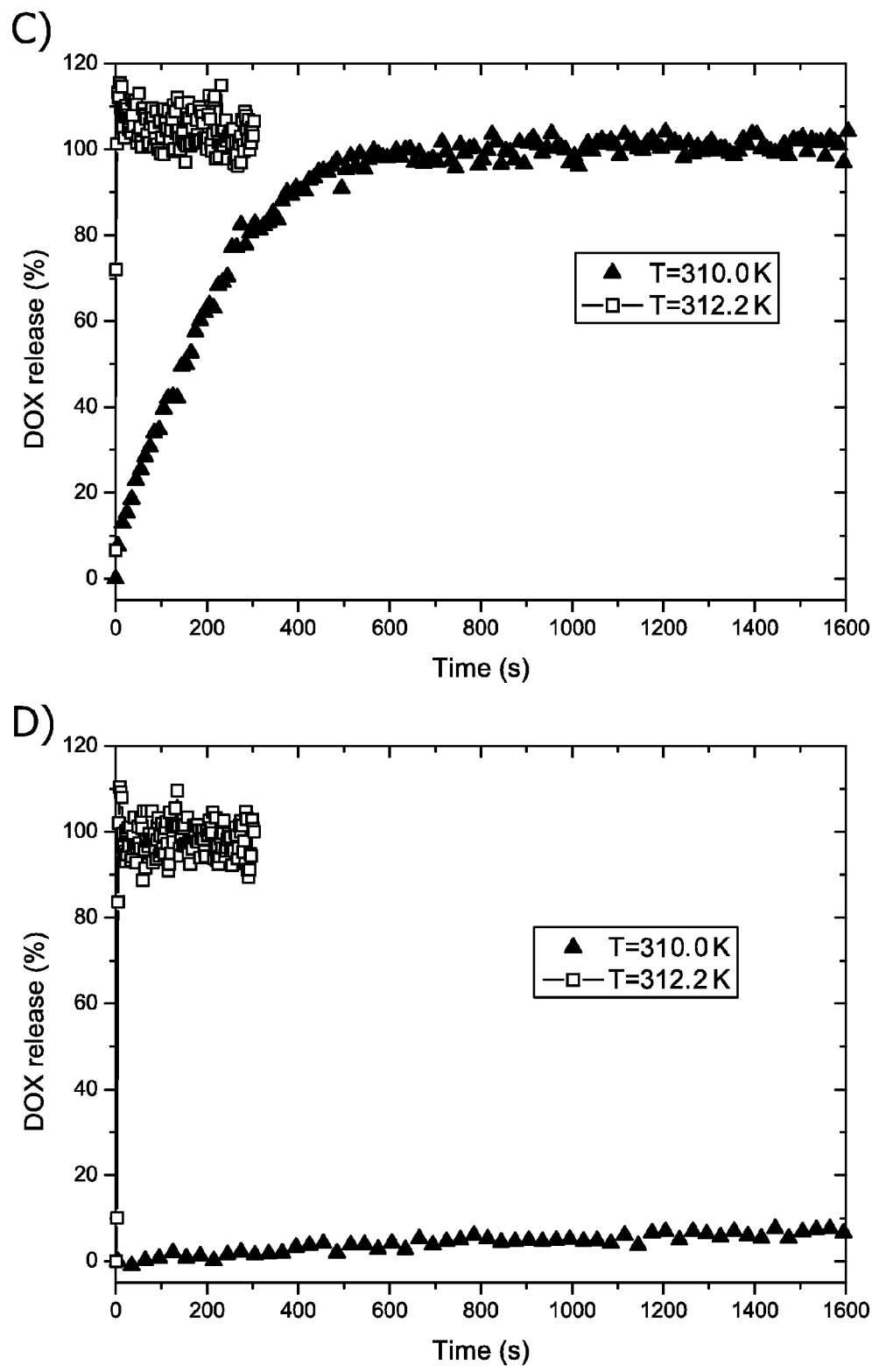
Figure 4:
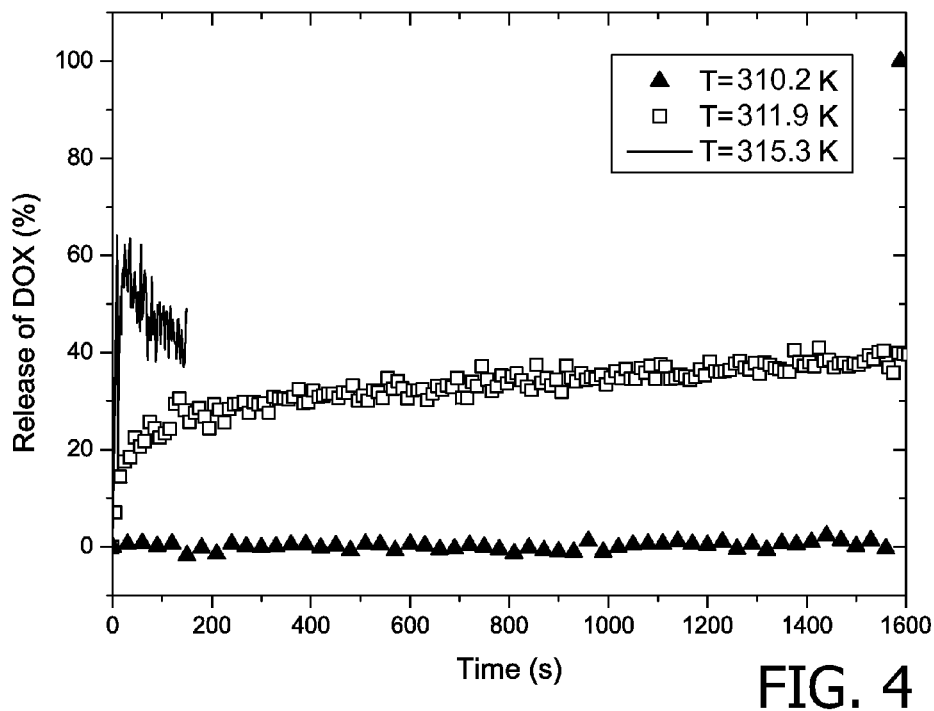
FIG. 4 shows the release of doxorubicin as a function of temperature for LTSLs containing of DPPC:DPPE-PEG2000, showing no quantitative release of doxorubicin.

A compound of the above-identified type $1_{n,R}$ having n=0, and R=$C_{17}H_{35}$, i.e. 1(n=0, R=$C_{17}H_{35}$), was prepared as follows. A solution of 4-dimethylaminopyridine (149.1 mg, 1.22 mmol) in dichloromethane (8 mL) dried on molecular sieves was added to 1-myristoyl-2-stearoyl-sn-glycero-3-phosphocholine, abbreviated as MSPC (211.8 mg, 0.404 mmol). Subsequently, acetic anhydride (115 µL, 1.23 mmol) was added and the mixture was stirred for 30 hours at room temperature under nitrogen atmosphere to yield a colorless solution. Methanol (8 mL) was added and the solvent was removed at room temperature under reduced pressure. The crude mixture was dissolved in chloroform (8 mL) and the organic layer was extracted three times with a solution of MeOH (8 mL) and 0.1 M HCl (8 mL). The mixture was centrifuged (30 minutes, 4000 rpm) to induce fast phase separation. The remaining organic layer was filtered, and then concentrated on a rotary evaporator at room temperature under reduced pressure. The crude product was dissolved in acetone (30 mL) and the solution was cooled to −20° C. to induce precipitation. To obtain the solid the mixture was centrifuged (30 minutes, 4000 rpm, −19° C.) and the solvent was decanted. The obtained product was washed with acetone, centrifuged (30 minutes, 4000 rpm, −19° C.) and dried with the aid of a nitrogen stream to obtain $1(n=0, R=C_{17}H_{35}$ (0.132 g) 58% Yield. The product was analyzed using $^1$H- and $^{13}$C NMR spectroscopy

EXAMPLE 2

The compound $1(n=3, R=C_{17}H_{35})$ was obtained similar to $1(n=0, R=C_{17}H_{35})$ of Example 1, in 70% yield (0.172 g) Instead of acetic anhydride, valeric anhydride (240 µL, 1.22 mmol) was used. This product did not dissolve completely in acetone therefore purification was done by stirring the crude product in acetone before cooling to −20° C. The product was analyzed using $^1$H- and $^{13}$C NMR spectroscopy.

EXAMPLE 3

Liposomes were formed by the lipid film hydration technique coupled with sequential extrusion. The phospholipids were dissolved in a solution of CHCl3/MeOH (4:1 v/v). The solvents were gently removed under reduced pressure and a thin lipidic film was obtained. The lipidic film was hydrated in a solution of 250 mM [Gd(hpdo3a)(H2O)] in 120 mM ammonium acetate buffer. The dispersion was extruded several times through polycarbonate membrane filters with pore diameters of 400, 200 and 100 nm, subsequently. After extrusion, the extraliposomal buffer was replaced by HEPES Buffered Saline (HBS), pH 7.4 (20 mM HEPES, 137 mM NaCl) by gel filtration through a PD-10 column (GE Healthcare). Subsequently, a doxorubicin solution in HBS (5 mg/mL) was added to the liposomes at a 20:1 phospholipid to doxorubicin weight ratio and incubated for 90 min at 37° C. Finally, the liposomes were passed through another PD-10 column to remove traces of non-encapsulated doxorubicin and free [Gd(hpdo3a)(H2O)].

The composition of the phospholipid bilayer is given in Table 1 below.

TABLE 1

| Formulation | Mixed short/long chain PC (all 10 mol %) | DPPC (mol %) | DPPE-PEG2000 (mol %) |
|---|---|---|---|
| A | $1_{n, R}$ (n = 0, R = $C_{15}H_{31}$) | 86 | 4 |
| B | $1_{n, R}$ (n = 0, R = $C_{17}H_{35}$) | 86 | 4 |
| C | $1_{n, R}$ (n = 1, R = $C_{17}H_{35}$) | 86 | 4 |
| D | $1_{n, R}$ (n = 2, R = $C_{17}H_{35}$) | 86 | 4 |
| E | $1_{n, R}$ (n = 3, R = $C_{15}H_{31}$) | 86 | 4 |
| F | $1_{n, R}$ (n = 3, R = $C_{17}H_{35}$) | 86 | 4 |
| G | 0 | 96 | 4 |

EXAMPLE 4

The liposomes of Example 3 were loaded with doxorubicin and 250 mM [Gd(hpdo3a)(H2O)]. The Tm and the hydrodynamic diameter of the liposomes (formulation A-E) were determined by differential scanning calorimetry (DSC) and dynamic light scattering (DLS), respectively. As shown in Table 2 and FIG. 1, the Tm of the phospholipid bilayer can be modulated by the incorporation of 1n,R.

TABLE 2

| Formulation | n | R | $T_m$ (K) | Diameter (nm) |
|---|---|---|---|---|
| A | 0 | $C_{15}H_{31}$ | 313.1 | 196 |
| B | 0 | $C_{17}H_{35}$ | 313.7 | 197 |
| C | 1 | $C_{17}H_{35}$ | 313.0 | 118 |
| D | 2 | $C_{17}H_{35}$ | 312.9 | 110 |
| E | 3 | $C_{15}H_{31}$ | 311.8 | 132 |
| F | 3 | $C_{17}H_{35}$ | 312.6 | 136 |
| G | — | — | 313.8 | 109 |

EXAMPLE 5

The release of doxorubicin and [Gd(hpdo3a)(H2O)] from the aqueous lumen of the liposomes was studied as a function of temperature probing the fluorescence at 590 nm and the longitudinal relaxivity (rl), respectively (FIGS. 2-6).

Figure 5:
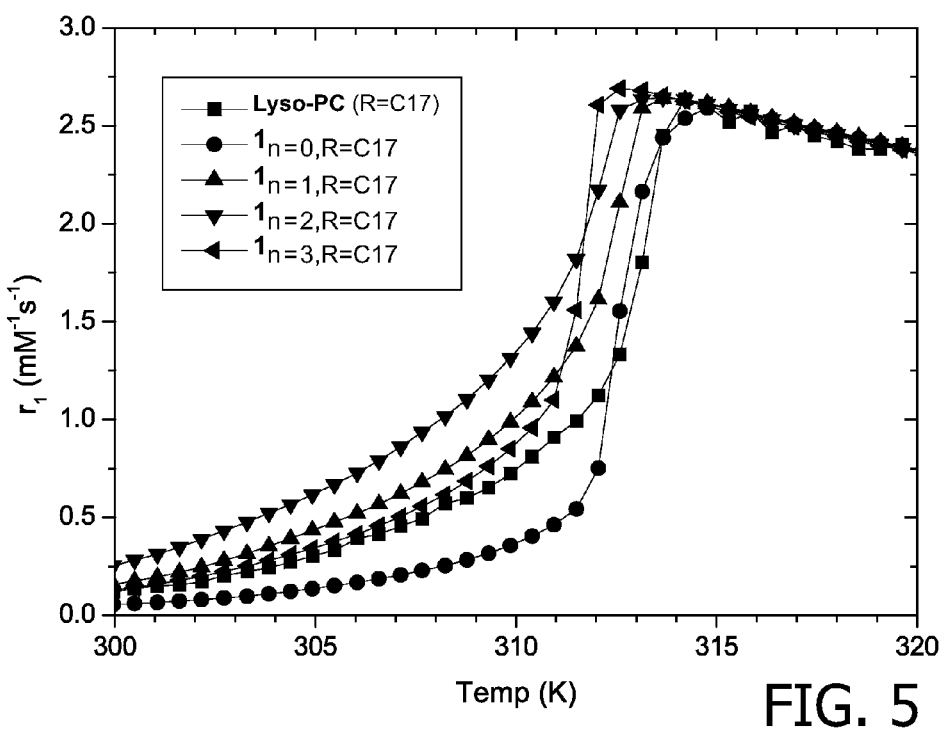
FIG. 5 shows the longitudinal relaxivity (rl) of temperature-sensitive liposomes containing 250 mM ProHance and doxorubicin during a linear temperature increase (0.5 K/min). At 310 K, the longitudinal relaxivity of paramagnetic liposomes containing $1_{0,R}$ (n=0 and R=$C_{17}H_{35}$) displays the lowest value. For the sake of legibility, a legend is contained in the Figure.
Figure 6:
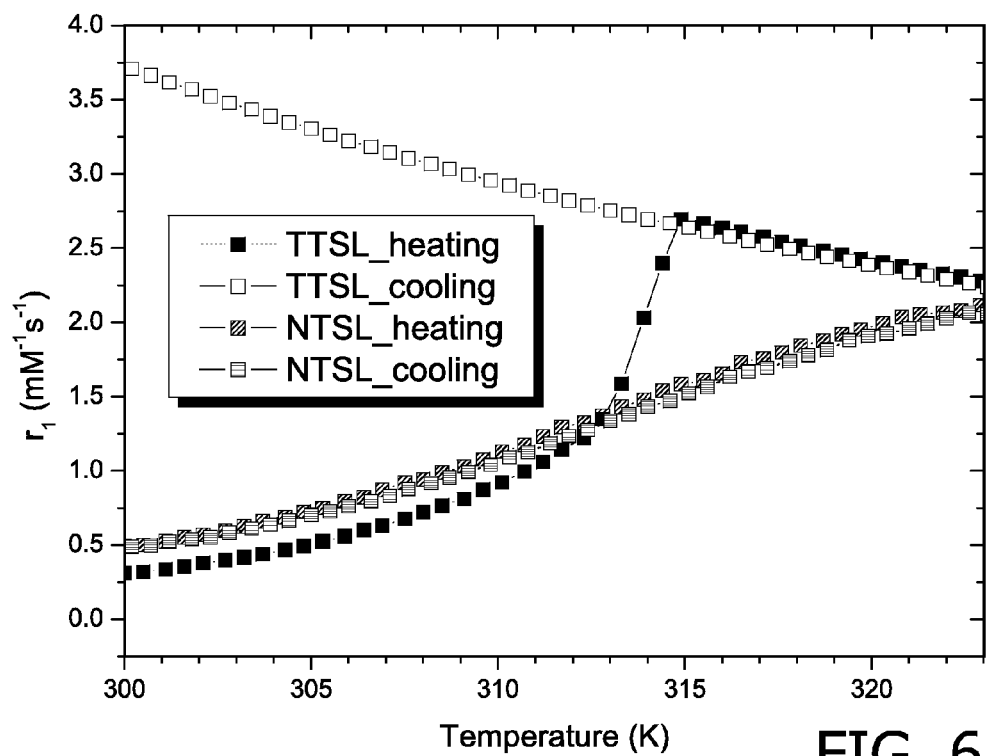
FIG. 6 shows the longitudinal relaxivity of liposomes (TTSL and NTSL) containing doxorubicin and 250 mM [Gd(hpdo3a)(H$_2$O)]. For the sake of legibility, a legend is contained in the Figure.
Figure 7:
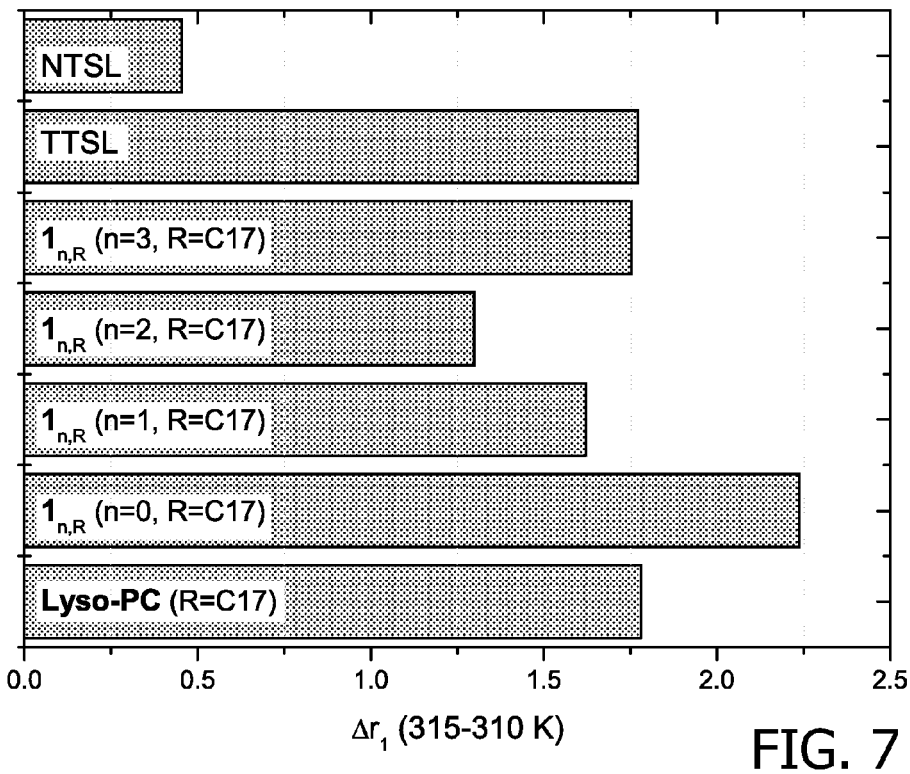
FIG. 7 shows the difference in the longitudinal relaxivity between 310 K and 315 K for liposomes encapsulating 250 mM ProHance and doxorubicin. Reference experiments have been performed with non-temperature sensitive liposomes (NTSL; HSPC:Chol:DPPE-PEG2000=75:20:3) and traditional temperature-sensitive liposomes (TTSLs; DPPC:HSPC:Chol:DPPE-PEG2000=50:25:15:3).

For all studied systems, the fluorescence of the encapsulated doxorubicin crystals is quenched at 300 K. However, at temperatures close to the Tm and upon the release from the liposome, a steep increase in the fluorescence signal is observed. As long as the MRI agent stays intraliposomal, the longitudinal relaxivity is limited by the transmembrane water exchange rate. When the temperature is raised the agent is released and MR contrast enhancement is observed. The incorporation of mixed short/long chain PCs in the bilayer allows one to tune the membrane properties that relate to drug release and the transmembrane water exchange rate and thereby the MR contrast enhancement (FIG. 5-7). By tuning the transmembrane water exchange rate, the properties of temperature-sensitive liposomes can be optimized for applications in MR image-guided drug delivery. Moreover, the co-encapsulation of doxorubicin and a T1-agent in a temperature-sensitive liposome consisting of mixed short/long chain PCs offers the opportunity to monitor the drug release process.

The invention claimed is:

1. A composition comprising a thermosensitive carrier having a semipermeable lipid bilayer shell, wherein the semipermeable lipid bilayer comprises a phospholipid having two terminal alkyl chains, one being a short chain having a chain length of at most five carbon atoms, the other being a long chain having a chain length of at least fifteen carbon atoms.

2. The composition of claim 1, wherein a difference in length between the short chain and the long chain is between eleven and sixteen carbon atoms.

3. The composition of claim 1, wherein the long chain has a length of at least sixteen carbon atoms.

4. The composition of claim 3, wherein the long chain has at most twenty carbon atoms.

5. The composition of claim 1, wherein the long chain has at most twenty carbon atoms.

6. The composition of claim 1, wherein the long chain has at most thirty carbon atoms.

7. The composition of claim 1, wherein the phospholipid is selected from the group consisting of phospholipids satisfying formula (I) and phospholipids satisfying formula (II),

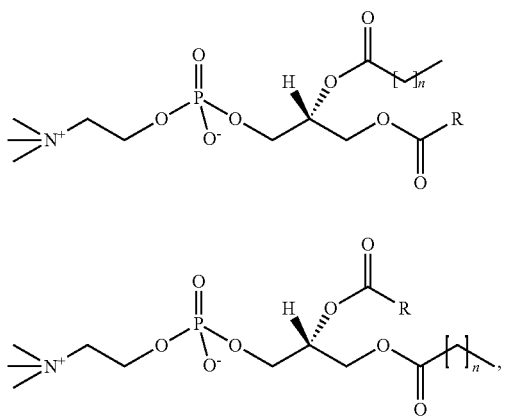

wherein R is an alkyl chain of fifteen to thirty carbon atoms, and n is an integer of 1 to 4.

8. The composition of claim 7, wherein R is selected from the group consisting of $C_{15}H_{31}$ and $C_{17}H_{35}$, and n is 1 to 4.

9. The composition of claim 1, further comprising at least one drug substance.

10. The composition of claim 1, further comprising at least one magnetic resonance imaging (MRI) contrast enhancing substance.

11. The composition of claim 1, further comprising:
at least one drug substance, and
at least one magnetic resonance imaging (MRI) contrast enhancing substance.

12. The composition of claim 1, further comprising a substance contained within the shell, wherein the carrier is configured for the in vivo release of the substance, and wherein the substance is selected from the group consisting of drugs, MRI contrast enhancing substances, and combinations thereof.

13. The composition of claim 1, wherein a membrane of the carrier includes a paramagnetic agent which is not a chemical shift reagent.

14. The composition of claim 13, wherein the carrier is aspherical.

15. The composition of claim 13, wherein the paramagnetic agent includes an amphiphilic compound comprising a lanthanide complex and having an apolar tail.

16. The composition of claim 1, further comprising a water solution of a paramagnetic shift reagent encapsulated within an interior compartment defined by the shell.

17. A method for magnetic resonance imaging (MRI) guided delivery of a drug to a subject, the method comprising:
administering to the subject a thermosensitive carrier comprising a semipermeable lipid bilayer shell, wherein the semipermeable lipid bilayer comprises a phospholipid having two terminal alkyl chains, one being a short chain having a chain length of at most five carbon atoms, the other being a long chain having a chain length of at least fifteen carbon atoms, the thermosensitive carrier carrying a drug and an MRI contrast enhancing substance;
allowing the carrier to release the drug and the MRI contrast enhancing substance; and
rendering a magnetic resonance image using the contrast provided by the contrast enhancing substance.

* * * * *